US008629183B2

(12) United States Patent
Caterson et al.

(10) Patent No.: US 8,629,183 B2
(45) Date of Patent: *Jan. 14, 2014

(54) METHODS FOR DECREASING CARTILAGE DAMAGE IN DOGS

(75) Inventors: Bruce Caterson, Cardiff (GB); Christopher Bond Little, St. Leonards (AU); John L. Harwood, Cardiff (GB); John Francis Innes, Wirral (GB); Dale A. Fritsch, Topeka, KS (US); Dennis Edward Jewell, Lawrence, KS (US); William David Schoenherr, Hoyt, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 137 days.

This patent is subject to a terminal disclaimer.

(21) Appl. No.: 12/820,813

(22) Filed: Jun. 22, 2010

(65) Prior Publication Data

US 2010/0256236 A1    Oct. 7, 2010

Related U.S. Application Data

(60) Division of application No. 11/057,718, filed on Feb. 14, 2005, which is a continuation-in-part of application No. 10/912,864, filed on Aug. 6, 2004.

(60) Provisional application No. 60/608,926, filed on Aug. 11, 2003.

(51) Int. Cl.
*A61K 31/20* (2006.01)
*A61K 31/201* (2006.01)
*A61K 31/202* (2006.01)
*A23K 1/18* (2006.01)

(52) U.S. Cl.
USPC .......................................... 514/560; 424/442

(58) Field of Classification Search
None
See application file for complete search history.

(56) References Cited

U.S. PATENT DOCUMENTS

| 3,683,076 | A | 8/1972 | Rovati |
| 4,843,095 | A | 6/1989 | Rubin |
| 4,895,725 | A | 1/1990 | Kantor et al. |
| 5,364,845 | A | 11/1994 | Henderson |
| 5,434,183 | A | 7/1995 | Larsson-Backstrom |
| 5,776,913 | A | 7/1998 | Ogilvie et al. |
| 5,840,715 | A | 11/1998 | Florio |
| 5,843,919 | A | 12/1998 | Burger |
| 5,916,565 | A | 6/1999 | Rose et al. |
| 6,015,798 | A | 1/2000 | Ogilvie et al. |
| 6,136,795 | A | 10/2000 | Florio |
| 6,162,787 | A | 12/2000 | Sorgente et al. |
| 6,297,280 | B1 | 10/2001 | Ishihara et al. |
| 6,331,567 | B1 | 12/2001 | Watson et al. |
| 6,344,220 | B1 | 2/2002 | Rose et al. |
| 6,399,105 | B1 | 6/2002 | Collin |
| 6,426,100 | B2 | 7/2002 | Watkins et al. |
| 6,432,929 | B1 | 8/2002 | Stone |
| 6,485,752 | B1 | 11/2002 | Rein |
| 6,552,081 | B1 | 4/2003 | Freedman et al. |
| 6,593,099 | B2 | 7/2003 | Xiao et al. |
| 6,638,525 | B2 | 10/2003 | Weidner |
| 6,645,948 | B2 | 11/2003 | Petito et al. |
| 2001/0044425 | A1 | 11/2001 | Ekanayake |
| 2001/0051184 | A1 | 12/2001 | Heng |
| 2001/0051206 | A1 | 12/2001 | Hayek et al. |
| 2002/0001640 | A1 | 1/2002 | Watkins et al. |
| 2002/0018828 | A1 | 2/2002 | Lepine |
| 2002/0068098 | A1 | 6/2002 | Babish et al. |
| 2002/0068718 | A1 | 6/2002 | Pierce |
| 2002/0076452 | A1 | 6/2002 | Babish et al. |
| 2002/0077299 | A1 | 6/2002 | Babish et al. |
| 2002/0164386 | A1 | 11/2002 | Meisner |
| 2003/0124219 | A1 | 7/2003 | Bui et al. |
| 2003/0147971 | A1 | 8/2003 | Myers |
| 2004/0068010 | A1 | 4/2004 | Zicker et al. |
| 2005/0057718 | A1 | 3/2005 | Chen et al. |
| 2006/0024356 | A1 | 2/2006 | Waldron et al. |
| 2006/0105931 | A1 | 5/2006 | Shi et al. |

FOREIGN PATENT DOCUMENTS

| AU | 2002311777 | 10/2002 |
| CN | 1557451 | 12/2004 |
| EP | 0678247 | 10/1995 |
| EP | 0713653 | 5/1996 |
| JP | 2006-528950 | 12/2006 |
| RU | 2112534 | 6/1998 |
| WO | WO 97/09982 | 3/1997 |
| WO | WO 97/21434 | 6/1997 |
| WO | WO 99/04782 | 2/1999 |
| WO | WO 00/21524 | 4/2000 |
| WO | WO 01/60356 | 8/2001 |

(Continued)

OTHER PUBLICATIONS

Clemmons et al., Research Support for Degenerative Myelopathy; Degenerative Myelopathy Funding; pp. 1,2 and 1-11.Updated Aug. 27, 2002, Accessed Feb. 12, 2007.
Mueller, R.S. et al. "A retrospective study regarding the treatment of lupoid onychodystrophy in 30 dogs and literature review" J. of the American Animal Hospital Assoc., vol. 39, No. 2, 2003, pp. 139-150.
Poole, A. Robin, "An introduction to the pathophysiology of osteoarthritis"; Frontiers in Biosciences 4; Oct. 15, 1999; pp. 662-670.
Richardson, D.C., et al., Vet. Clin. North Amer. Small Animal Practice 27:883-911, 1997.
Schoenherr, W.D., et al. in Small Animal Clinical Nutrition 4th Ed., Hand et al. Eds., Walsworth Publishing Company, Marceline, MO, 907-921,2000.

(Continued)

Primary Examiner — Sreeni Padmanabhan
Assistant Examiner — Jody Karol
(74) Attorney, Agent, or Firm — Thomas M. Hunter

(57) ABSTRACT

A method for modulating enzymatic degradation of articular cartilage in a dog comprises administering to the dog an enzymatic degradation modulating effective amount of eicosapentaenoic acid (EPA), for example as a component of a food composition. By practice of the method in a dog having arthritis, mobility of the dog can be increased, weight bearing in an arthritic limb can be increased, and/or pain associated with arthritis can be reduced.

6 Claims, No Drawings

(56) References Cited

FOREIGN PATENT DOCUMENTS

| WO | WO 01/82720 | 11/2001 |
|---|---|---|
| WO | WO 03/075670 | 9/2003 |
| WO | WO 2004/006688 | 1/2004 |
| WO | WO 2005/018630 | 3/2005 |
| WO | WO 2005/117603 | 12/2005 |
| WO | WO 2006/002976 | 1/2006 |

OTHER PUBLICATIONS

Volker, D., et al, Efficacy of Fish Oil Concentrate in the Treatment of Rheumatoid Arthritis, The Journal of Rheumatology, 27:2343-2346, 2000.
Volker, D.H., et al., The Eicosapentaenoic to Docosahexaenoic Acid Ratio of Diets Affects the Pathogenesis of Arthritis in Lew/SSN Rats, Am. Soc. For Nutr. Sci., 559-565,2000.
Wander et al., "The Ratio of Dietary (n-6) to (n-3) Fatty Acids Influences Immune System Function, Eicosanoid Metabolism, Lipid Proxidation and Vitamin E Status in Aged Dogs"; American Society for Nutritional Sciences; 1997.
Youdim et al., "Essential fatty acids and the brain: possible health implications"; International Journal of Developmental Neuroscience; 2000; pp. 383-399.
Beale, B., "Use of nutraceuticals and chodroprotectants in osteoarthritic dogs and cats," Vet Clin Small Animal Practice 34 (2004) pp. 271-289.
Geels, J.J. et al., "Evaluation of a High N-3 Fatty Acid Diet for the Treatment of Degenerative Joint Disease of the Canine Stifle," Veterinary Surgery, Lippincot, vol. 29, No. 5, 2000, p. 462.
Bierer et al., Improvement of Arthritic Signs in Dogs Fed Green-Lipped Mussel (Perna canaliculus), J. Nutri. 132:1634S-1636S, 2002.
Budsberg, S. Effects of fatty acid supplementation on the development of osteoarthritis in dogs: biochemical, clinical and radiographic evaluation Abstracts of the Frist World Ortho. Vet. Cong., 2002, pp. 56-57.
Caterson et al., Mechanisms involved in cartilage proteoglycan catabolism, Matrix Biology 19:333-344, 2000.
Clemmons et al., Research Support for Degenerative Myelopathy; Degenerative Myelopathy Funding; pp. 1, 2 and 1-11, 1997, Accessed on Feb. 12, 2007.
Curtis, C.L. et al., Effects of $n$-3 fatty acids on cartilage metabolism, Proc. Of Nutr. Soc., 61:381-389, 2002.
Curtis, C.L., Biological basis for the benefit of nutraceutical supplementation in arthritis, Drug Discovery Today, 9:4, 165-172, 2004.
Hansen, A.A., $N$-3 fatty acids decrease inflammatory mediators in arthritic dogs, FASEB J. 17:A330 (Abstract #200.3), 2003.
Hedbom et al., "Molecular aspects of pathogenesis in osteoarthritis: the role of inflamation"; CMLS Cellular and Molecular Life Sciences,; vol. 591, 2002£ 12ages 45-53.
Kremer, J.M., et ai, Effects of Manipulation of Dietary Fatty Acids on Clinical Manifestations of Rheumatoid Arthritis, The Lancet, 184-187, Jan. 26, 1985.
Kremer, J.M., $n$-3 Fatty acid supplements in rheumatoid arthritis, Am J Clin Nutr, 71 (suppl):349S-351 S, 2000.
Lands, W.E., Biochemistry and physiology of $n$-3 fatty acids, The FASEB Journal 6:2530-2536m 1992.
Miller WH, et al., Treatment of dogs with hip arthritis with a fatty acid supplement. Canine Practice 17(6): 6-8, 1992.
Nesbitt, GH, et al, Effect on $n$-3 fatty acid ratio and dose on clinical manifestations, plasma fatty acids and inflammatory mediators in dogs with pruritus, Veterinary Dermatology, 14:67-74, 2003.
Adam, 2003, "Dietary fatty acids and immune reactions in synovial tissue," European Journal of Medical Research 8(8):381-387.
Adan et al., 1999, "Effects of docosahexaenoic and eicosapentaenoic acid on lipid metabolism, eicosanoid production, platelet aggregation and atherosclerosis in hypercholesterolemic rats," Bioscience, Biotechnology and Biochemistry 63(1):111-119.
Borras et al., 1999, "Age-related changes in the brain of the dog," Vet. Pathol. 36(3):202-211.
Brigelius-Flohe et al., 1999, "Vitamin E: Function and Metabolism," FASEB J. 13:1145-1155.
Bui et al., 2001, "Influence of green lipped mussels (Perna canaliculus) in alleviating signs of arthritis in dogs," Vet. Ther. 2(2):101-111.
Calder et al., 2001, "Polyunsaturated fatty acids and rheumatoid arthritis," Curr. Opin. Clin. Nutr. Metab. Care 4(2):115-121.
Cao et al., 1998, "Increases in Human Plasma Antioxidant Capacity after Consumption of Controlled Diets High in Fruit and Vegetables," Amer. J. Clin. Nutr. 68:1081-1087.
Chin et al., 1990, "Effect of lipoxygenase products on glycosaminoglycan (GAG) synthesis by cultured chondrocytes," Clin. Rheumatol. & Related Res. 3(4):265-271.
Cummings et al., 1996, "The Canine As an Animal Model of Human Aging and Dementia," Neurobiol. Of Aging 17:259-268.
Curtis et al., 2003, "The effect of $n$-3 (omega-3) polyunsaturated fatty acids on degenerative joint disease," Database FSTA Online! International Food Information Service AN: 2003-00-a2058 Abstract; Agro Food Industry Hi Tech 14(3):61-69.
De Vizia et al., 2003, "Effect of an 8-month treatment with omega-3 fatty acids (eicosapentaenoic and docosahexaenoic) in patients with cystic fibrosis," Journal of Parenteral and Enteral Nutrition 27(1):52-57.
Frei, 1999, "Molecular and Biological Mechanisms of Antioxidant Action," FASEB J. 13:963-964.
Fujimoto et al., 1989, "The effect of dietary docosahexaenoate on the learning ability of rats," in: Health Effects of Fish and Fish Oils, Chandra, ed., ARTS Biomedical Publishers and Distributors, St. John's, Newfoundland, pp. 275-284.
Hagen et al., 1999, "(R)-alpha-lipoic acid-supplemented old rats have improved mitochondrial function, decreased oxidative damage, and increased metabolic rate," FASEB J. 13(2):411-418.
Hansen et al., 2003, "$N$-3 fatty acids decrease inflammatory mediators in arthritic dogs," Exp. Biol.: Translating the Genome, Abstract #3146, San Diego, CA.
Harman, 1993, "Free Radical Theory of Aging: A Hypothesis on Pathogenesis of Senile Dementia of the Alzheimer's Type," Age 16:23-30.
Head et al., 1995, "Spatial Learning and Memory as a Function of Age in the Dog," Behavioral Neurosci. 109(5):851-858.
International Search Report and Written Opinion in International Application No. PCT/US04/025759, mailed Dec. 7, 2004.
International Search Report and Written Opinion in International Application No. PCT/US06/004858, mailed Mar. 6, 2007.
James et al., 1997, "Dietary $n$-3 fatty acids and therapy for rheumatoid arthritis," Seminars in Arthritis and Rheumatism 27(2):85-97.
Jones et al., 1997, "Evidence for the involvement of docosahexaenoic acid in cholinergic stimulated signal transduction at the synapse," Neurochemical Research 22(6):663-670.
Leveque, 1998, "Cognitive Dysfunction in Dogs, Cats an Alzheimer's-Like Disease," J. Amer. Vet. Med. Assoc. 212(9):1351.
Lovell et al., 1998, "Elevated 4-Hydroxynonenal in Ventricular Fluid in Alzheimer's Disease," Neurobiol. Of Aging 18:457-461.
Markesbery et al., 1998, "Four-Hydroxnonenal, a Product of Lipid Peroxidation, Is Increased in the Brain in Alzheimer's Disease," Neurobiol. Of Aging 19:33-36.
McGahon et al., 1999, "Age-related changes in oxidative mechanisms and LTP are reversed by dietary manipulation," Neurobiology of Aging 20(6):643-653.
McGahon et al., 1999, "Age-related changes in synaptic function: analysis of the effect of dietary supplementation with omega-3 fatty acids," Neuroscience 94(1):305-314.
Milgram et al., 1994, "Cognitive Functions and Aging in the Dog: Acquisition of Nonspatial Visual Tasks," Behavioral Neurosci. 108(1):57-68.
Milgram et al., 1999, "Landmark Discrimination Learning in the Dog," Learning & Memory 6(1):54-61.
National Research Council, 2006, Nutrient Requirements of Dogs and Cats, pp. 359-360.
Reisbick et al., 1997, "Omega-3 fatty acidy deficiency and behavior," Chapter 17 in Handbook of Essential Fatty Acid Biology: Biochemistry, Physiology and Behavior Neurobiology, pp. 397-426.

(56) References Cited

OTHER PUBLICATIONS

Rogers, 2001, "A healthy body, a healthy mind: long-term impact of diet on mood and cognitive function," Proceedings of the Nutrition Society 60(1):135-143.

Saito et al., 1983, "In vitro effect of EPA on the metabolism of [1-$^{14}$C] arachidonic acid in rat peritoneal macrophages," The 2nd Department of Internal Medicine, School of Medicine, Chiba University, Chiba 280, Japan 623:162-170.

Sano et al., 1997, "A Controlled Trial of Selegiline, Alpha-Tocopherol, or Both as Treatment for Alzheimer's Disease. The Alzheimer's Disease Cooperative Study," New England J. Med. 336(17):1216-1222.

Schoenherr et al., 1997, "Nutritional modification of inflammatory diseases," Seminars in Veterinary Medicine and Surgery (Small Animal) 12(3):212-222.

Stammers et al., 1989, "Fish oil in osteoarthritis," Lancet 2(8661):503.

Tomobe et al., 2000, "Dietary docosahexaenoic acid suppresses inflammation and immunoresponses in contact hypersensitivity reaction in mice," Lipids 35(1):61-69.

Van Haaster et al., 1993, "Formation of prostanoids and hydroxy fatty acids by stimulated peritoneal mast cells: role of the dietary fat type in rat," Biochimica et Biophysica Acta. 1167(2):147-154.

Weaver et al., 1988, "Health effects and metabolism of dietary eicosapentaenoic acid," Prog. Food Nutr. Sci. 12(2):111-150.

www.DRNANCYSPLACE.com/myelopathy.htm, 2007.

www.ETHICALNUTRIENTS.com/au/content/products/fish-oil, 2008.

www.GOVITA.com/au/library/Nutritionals/NutritionalsFishOil. pdf, unknown publication date.

Miller et al., 1989, "Clinical Trial of DVM Derm Caps in the Treatment of Allergic Disease in Dogs: A Nonblinded Study," J. Amer. Animal Hospital Assoc. 25(2):163-168.

METHODS FOR DECREASING CARTILAGE DAMAGE IN DOGS

This application is a divisional of U.S. patent application Ser. No. 11/057,718 filed Feb.14, 2005, which is a continuation in part of U.S. patent application Ser. No. 10/912,864, filed Aug. 6, 2004, which claims priority of U.S. patent application Ser. No. 10/638,832, filed Aug. 11, 2003 and converted to a provisional application, Ser. No. 60/608,926, on Aug. 5, 2004. The above-cited applications are incorporated herein by reference in their entirety.

FIELD OF THE INVENTION

The present invention relates to methods of managing arthritis and arthritis-related conditions in companion animals, more particularly dogs.

BACKGROUND OF THE INVENTION

Arthritis, more particularly osteoarthritis, is a degenerative joint disease commonly occurring in humans and in companion animals. See for example Richardson et al. (1997), *Vet. Clin. North Amer. Small Animal Practice* 27, 883-911.

Osteoarthritis involves progressive deterioration of articular cartilage, with loss of proteoglycan and collagen and proliferation of new bone, accompanied by a variable inflammatory response within the synovial membrane. It is the most common form of joint and musculoskeletal disease affecting dogs but is relatively uncommon in cats. See for example Schoenherr et al. (2000) in Hand et al., eds.: *Small Animal Clinical Nutrition,* 4th ed., 907-921, Walsworth Publishing Co., Marceline, Mo.; Hedborn et al. (2002) *Cell Mol. Life Sci.* 59, 45-53; Pool (1999) *Front. Biosci.* 4, D662-D670.

Management of osteoarthritis can include pharmacological treatments, surgery, nutraceutical administration and diet management. Such current management approaches have, however, focused on symptomatic relief and as such they have not been entirely successful in disease management or in treating the underlying pathologies. Hence there remains a continuing need for new approaches in managing osteoarthritis in companion animals, more particularly dogs.

Omega-3 (also known as n-3) fatty acids are needed in diets of mammals. They are naturally occurring materials in foods and have been used in dietary supplements. Schoenherr et al. (2000), supra, reviewed use of fatty acids including n-3 fatty acids in inflammatory disease including arthritis, and referenced a compilation by Miller et al. (1992) *Canine Practice* 17(6), 6-8, of observations of dog owners who perceived improvement in clinical signs of arthritis in their dogs when treated with fatty acids for dermatological problems.

Three omega-3 fatty acids are currently of most interest as dietary components: eicosapentaenoic acid (EPA), docosahexaenoic acid (DHA) and alpha-linolenic acid (ALA). Hitherto no great distinction has been drawn among these three.

SUMMARY OF THE INVENTION

It has now been found that, in the canine, omega-3 fatty acids are not equal in their activity in arthritic conditions where cartilage is involved. In studies reported herein, only EPA, but not DHA or ALA, was absorbed appreciably by canine cartilage, and cartilage damage as measured by glycosaminoglycan (GAG) release was significantly lowered after exposure to EPA, but not DHA or ALA. Benefits of administering the specific omega-3 fatty acid EPA to a dog having arthritis can include increased mobility of the dog, increased weight bearing in a limb of the dog, and reduced pain associated with the arthritis.

Accordingly there is now provided a method for increasing mobility of a dog having arthritis, the method comprising administering to the dog EPA in an amount effective to decrease cartilage damage in the dog.

There is further provided a method for increasing weight bearing in a limb of a dog having arthritis, the method comprising administering to the dog EPA in an amount effective to decrease cartilage damage in the dog.

There is still further provided a method for reducing pain associated with arthritis in a dog, the method comprising administering to the dog EPA in an amount effective to decrease cartilage damage in the dog.

In a further embodiment of the invention, there is provided a method for modulating enzymatic degradation of articular cartilage in a dog, the method comprising administering to the dog an enzymatic degradation modulating effective amount of EPA.

According to the above methods, the EPA can be administered by various routes, including orally as a component of a food composition.

Further advantages and benefits of the present invention will be apparent to one skilled in the art from reading this specification.

DETAILED DESCRIPTION

This invention involves administration of EPA as a method of managing osteoarthritic diseases and conditions, and symptoms thereof, in dogs.

Omega-3 fatty acids are a recognized group of polyunsaturated long-chain (generally 12-26 carbon atoms) carboxylic acids. The physiologically more important omega-3 fatty acids have unbranched chains that are 18-22 carbon atoms in length. All have a double bond between the 3rd and 4th carbon atoms as counted from the methyl (omega) end of the molecule. Eicosapentaenoic acid (EPA) has a chain length of 20 carbon atoms and has a total of five double bonds, including one at the omega-3 position.

When an omega-3 fatty acid, in particular EPA, is mentioned herein, it will be understood that derivatives thereof, known to those of skill in the art, can be substituted if desired. Examples of suitable derivatives include esters, such as branched or unbranched and/or saturated or unsaturated $C_1$-$C_{30}$ alkyl or cycloalkyl esters, in particular $C_1$-$C_6$ alkyl esters, of omega-3 fatty acids, particularly EPA.

EPA can be administered to a dog by one or more of many routes of administration, such as, for example, oral, intranasal, parenteral (e.g., intravenous or subcutaneous) routes and the like. The oral route is particularly suitable and EPA can be administered orally in a nutraceutical or pharmaceutical dosage form or as a component of a food composition.

When present in a food composition, which can be wet or dry, EPA can be incorporated therein, for example by any suitable mixing procedure, and/or distributed on the surface of food pieces, for example by spraying, agglomerating, dusting or precipitating on the surface. In particular embodiments EPA is present in a food composition providing the nutritional diet per se, in a snack, supplement or treat, or in a liquid portion of the diet such as water or another fluid.

EPA can alternatively be administered in solid faun such as a powder, or in liquid or gel form, or in a nutraceutical or pharmaceutical dosage form such as a capsule, tablet, caplet, syringe or the like. Within such a dosage form the EPA can be present in solid, liquid or gel form. Any of the usual nutraceutical or pharmaceutical carriers can be employed together with the EPA, including water, glucose, sucrose and the like.

In certain embodiments, EPA-containing food compositions are administered that are essentially free of DHA and/or ALA. "Essentially free of DHA and/or ALA" is intended to mean that either or both of DHA and ALA are substantially absent or that there are only small and insignificant amounts of either or both of DHA or ALA present, for example, less than about 0.1%, less than about 0.03%, less than about 0.01%, less than about 0.003% or less than about 0.001%, by weight of the composition. In embodiments that are "essentially free of DHA and/or ALA" herein, any amount of DHA and/or ALA present is at a concentration sufficiently low so that no substantial incremental effect is produced in an osteoarthritic dog on osteoarthritis or the progression thereof or symptoms produced thereby.

In other embodiments, present with the EPA can be other omega-3 fatty acids such as DHA and ALA in significant quantities. In some embodiments, omega-6 fatty acids such as linoleic acid, gamma-linolenic acid (GLA) and/or especially arachidonic acid (AA), can also be present. Omega-3 and omega-6 fatty acids can be found in sources such as fish oils and fish meals in relatively large quantities. According to the present invention, the benefits in decreasing cartilage damage by administration of a mixture of omega-3 fatty acids, or a mixture of omega-3 and omega-6 fatty acids, are attributable largely or essentially wholly to EPA. In any such mixture, therefore, it is important that EPA be present in an amount effective to decrease cartilage damage in a dog.

EPA administered according to the present method is effective against various forms of osteoarthritis as well as other forms of arthritis including rheumatoid arthritis.

EPA acts to inhibit development of the degenerative process in joint cartilage or to diminish the degenerative process and thereby improve joint health in osteoarthritic dogs or in dogs that might otherwise develop osteoarthritis. This effect is in addition to any anti-inflammatory action of omega-3 fatty acids, which may be of less importance in canine osteoarthritis because of limited involvement of inflammation in the osteoarthritis.

Use of an in vitro explant procedure involving articular cartilage as shown in the examples below, demonstrated that, of EPA, DHA and ALA, the only omega-3 fatty acid to significantly decrease induced release of glycosaminoglycan (GAG) from the cartilage was EPA. GAGs are a structural component of proteoglycan, therefore, release of GAG indicates degradation of proteoglycan.

With respect to prevention of joint damage from osteoarthritis, a particular target group of dogs comprises those in need of such preventive care. For example, large breeds such as labrador retriever, rottweiler, German shepherd and the like are more susceptible to osteoarthritis as demonstrated by its greater occurrence in these breeds. Additionally, dogs above the age of about 6 years have a significantly greater occurrence of osteoarthritis. Active dogs, athletic dogs and obese dogs can also be at risk.

The quantity of EPA to be administered can vary substantially. As shown in examples herein, an actual dose response is observed—the greater the amount of EPA administered, the greater the anti-arthritic effect. Generally, a minimum of at least about 0.2% by weight of a nutritious diet satisfying ordinary daily requirements of a dog is required. In various embodiments, at least about 0.2%, at least about 0.25%, at least about 0.3%, at least about 0.4%, at least about 0.5% or at least about 0.6% by weight of the diet can be used. Suitably the diet can contain, in various embodiments, up to about 5%, up to about 4%, up to about 3%, up to about 2.5%, up to about 2.25% or up to about 2% by weight EPA. All percentages by weight herein, unless otherwise specified, are on a dry matter basis.

A specific amount of EPA can be included in the usual food ration on a daily basis, or the same amount can be provided to the animal in a treat or supplement on a daily basis. A combination of these or any other dosing means can be employed as long as an effective quantity of EPA is provided daily.

In mixtures of omega-3 and omega-6 fatty acids, the weight ratio of omega-3 to omega-6 fatty acid can vary significantly. In various embodiments, the omega-6 to omega-3 weight ratio can be about 1.1:1 to about 0.2:1 or about 1.08:1 to about 0.42:1; for example about 0.2:1, about 0.25:1, about 0.3:1, about 0.4:1, about 0.5:1, about 0.6:1, about 0.8:1, about 1.0:1, or greater. In various embodiments, the omega-6 to EPA weight ratio can be about 12.5:1 to about 1.0:1 or about 12.4:1 to about 1.12:1, for example about 0.2:1, about 025:1, about 0.3:1, about 0.4:1, about 0.5:1, about 0.6:1, about 0.8:1, about 1.0:1, about 1.5:1, about 2:1, about 2.5:1, about 3:1, about 4:1, about 5:1, about 6:1, about 7.5:1, about 10:1, about 12.5:1, or greater. In various embodiments, the arachidonic acid (AA, an omega-6 fatty acid) to EPA weight ratio can be about 2.8:1 to about 0.01:1 or about 0.28:1 to about 0.08:1, for example about 0.01:1, about 0.02:1, about 0.04:1, about 0.06:1, about 0.08:1, about 1.0:1, about 1.5:1, about 2.8:1, or greater.

The EPA can be administered in amounts calculated as mg/kg body weight. Thus, for example, a 20 kg dog consumes a daily diet of about 275 g of food per day. Amounts of EPA in the diet of about 0.2%, about 0.3%, about 0.4%, about 0.5% or about 0.6% by weight would result in administering to such a dog about 27.5, about 41.25, about 55, about 68.75 or about 82.5 mg/kg body weight respectively. More particularly, EPA can be administered to a dog in an amount of about 20 to about 150 mg/kg body weight, for example about 20, about 28, about 30, about 40, about 41, about 50, about 55, about 60, about 69, about 70, about 80, about 82, about 90, about 100, about 120 or about 150 mg/kg body weight, or greater.

Foods are generally classified in the pet food industry as "wet" or "dry". A wet food has a relatively high amount of water and is usually presented in a can or other container wherein air is substantially or totally excluded. Examples of such foods are "chunk and gravy" compositions, compositions having individual solid particles in the presence of a liquid gravy, and loaf-type compositions, which generally take the shape of the container. Dry foods are generally baked or extruded materials, the latter then cut into individual shaped portions, usually known as kibbles. EPA is readily incorporated into a wet food through conventional means. Encapsulation can be employed to protect EPA from air oxidation in a dry food. Additionally, use of antioxidants and nitrogen sweeps of packaging can also be employed. This is exemplified by U.S. Pat. No. 4,895,725 which has special emphasis on micro-encapsulation of specific fish oils. Oils which have high levels of omega-3 fatty acids include oils of menhaden, salmon, cod and the like.

The present invention also provides, in various embodiments, methods involving administration of a composition comprising EPA to a dog for reducing the severity and frequency of clinical signs of osteoarthritis and the pain associated with this disease without substantial adverse reactions or side effects. Additionally, in various embodiments, the invention provides a method of slowing the clinical progression of an osteoarthritic condition of a dog, the method comprising administration of a composition comprising EPA. In various embodiments, a method as described herein substantially improves the overall osteoarthritic condition of the dog so that this benefit can be objectively measured through increased weight bearing in osteoarthritic limbs. The present invention also provides methods involving administration of EPA in combination with other treatment modalities for osteoarthritis, including administration of various anti-arthritic medicaments and/or feeding the animal a weight management diet, both of which are known in the art.

It is believed that the effect of EPA in decreasing cartilage damage associated with osteoarthritis can occur at least in part through down-regulation of one or more genes responsible for cartilage degradation. In some cases, one or more genes responsible for cartilage degradation can be turned off. According to an embodiment of the invention, mRNA message expression in cartilage tissue of the dog for an enzyme causing cartilage degradation, for example an aggrecanase, is reduced. Decreased cartilage damage can be indicated by a decrease in induced release of glycosaminoglycan (GAG) from cartilage tissue.

Thus the following are further embodiments of the invention:

A method of down-regulating one or more genes related to enzymatic degradation of articular cartilage in a dog, the method comprising administering to the dog a gene down-regulating effective amount of EPA.

A method for turning off one or more genes related to enzymatic degradation of articular cartilage in a dog, the method comprising administering to the dog a gene turning-off effective amount of EPA.

A method for reducing mRNA message expression in cartilage tissue of a dog for an enzyme, e.g., an aggrecanase, causing cartilage degradation, the method comprising administering to the dog an mRNA message expression reducing effective amount of EPA.

A method for decreasing induced release of GAG from cartilage tissue of a dog, the method comprising administering to the dog a GAG release decreasing effective amount of EPA.

EXAMPLES

The following examples are merely illustrative, and do not limit this disclosure in any way.

Example 1

This example illustrates the release of glycosaminoglycan (GAG) as effected by omega-3 fatty acids in cultured canine cartilage tissue.

Articular cartilage was obtained from left and right stifles (both femoral condyles and tibial plateau) of four dogs. Cartilage explants were cultured for 3 days in a medium with 10% fetal bovine serum, then washed 3 times in a serum-free medium. Explants were then cultured for 6 days in a serum-free medium containing 0, 100 or 300 µg/ml n-3 fatty acid (EPA, ALA or DHA). After this period, all explants were washed 3 times in a fatty acid-free, serum-free medium. Explants were then cultured individually in triplicate for 4 days in 1 ml fatty acid-free, serum-free medium containing no additives (control, C), $10^{-6}$M retinoic acid (RA) or 50 ng/ml oncostatin M (OSM). Note that not all treatments were possible on all dogs because of cartilage availability. The release of GAG into the medium was measured (µg/mg wet weight) at the termination of culture. In the tables below, the mean and standard deviation (SD) of GAG release are given for the triplicate cultures from each of the four dogs. In addition, the media lactate concentrations (µg/mg wet weight) are given for each treatment.

TABLE 1

Results for Dog 1

| Treatment | n | GAG release | | | | lactate | |
|---|---|---|---|---|---|---|---|
| | | mean | SD | min | max | mean | SD |
| C | 3 | 1.36 | 0.50 | 0.85 | 1.84 | 26.07 | 33.7 |
| C + carrier | 3 | 1.63 | 0.31 | 1.31 | 1.92 | 21.95 | 22.6 |
| C + 100 EPA | 3 | 1.59 | 0.29 | 1.29 | 1.87 | 23.85 | 25.4 |
| C + 300 EPA | 3 | 1.04 | 0.53 | 0.57 | 1.61 | NA** | NA** |
| RA | 3 | 10.50 | 1.84 | 8.89 | 12.50 | 36.00 | 39.3 |
| RA + carrier | 3 | 7.15 | 4.53 | 2.00 | 10.50 | 33.07 | 45.4 |
| RA + 100 EPA | 3 | 8.68 | 2.00 | 6.61 | 10.60 | 29.37 | 34.8 |
| RA + 300 EPA | 3 | 1.59 | 1.70 | 0.44 | 3.54 | 26.40 | 39.1 |
| OSM | 3 | 13.60 | 1.56 | 12.60 | 15.40 | 25.37 | 30.8 |
| OSM + carrier | 3 | 14.25 | 6.44 | 7.35 | 20.10 | 27.40 | 33.8 |
| OSM + 100 EPA | 3 | 6.29 | 2.30 | 4.34 | 8.80 | 33.57 | 52.5 |
| OSM + 300 EPA | 3 | 2.17 | 1.93 | 0.93 | 4.39 | 20.05 | 23.8 |

**not analyzed

As shown in Table 1, significant decrease in GAG release occurred with 100 µg/ml EPA in OSM treated cultures and with 300 µg/ml in RA and OSM treated cultures. There was no significant decrease in media lactate concentrations with any dose of EPA.

TABLE 2

Results for Dog 2

| Treatment | n | GAG release | | | | lactate | |
|---|---|---|---|---|---|---|---|
| | | mean | SD | min | max | mean | SD |
| C + carrier | 3 | 0.50 | 0.42 | 0.13 | 0.96 | 22.80 | NA** |
| C + 100 EPA | 3 | 0.34 | 0.33 | 0.10 | 0.72 | 39.52 | 24.57 |
| C + 300 EPA | 3 | 0.57 | 0.46 | 0.25 | 1.10 | 39.20 | 13.86 |
| OSM + carrier | 3 | 11.70 | 5.11 | 7.10 | 17.20 | 26.90 | 4.77 |
| OSM + 100 EPA | 3 | 5.25 | 3.00 | 2.19 | 8.19 | 21.70 | 9.84 |
| OSM + 300 EPA | 3 | 2.83 | 0.23 | 2.66 | 3.09 | 16.23 | 3.60 |
| C + carrier | 3 | 0.97 | 0.22 | 0.84 | 1.23 | 17.40 | NA** |
| C + 100 DHA | 3 | 0.64 | 0.31 | 0.45 | 1.00 | 21.00 | 6.26 |
| C + 300 DHA | 3 | 0.84 | 0.36 | 0.43 | 1.10 | 36.20 | NA** |
| OSM + carrier | 3 | 8.7 | 0.78 | 8.10 | 9.60 | 25.33 | 7.11 |
| OSM + 100 DHA | 3 | 8.57 | 4.22 | 3.70 | 11.20 | 28.13 | 2.72 |
| OSM + 300 DHA | 3 | 6.07 | 4.03 | 3.18 | 10.70 | 24.80 | 1.95 |
| C + carrier | 3 | 0.82 | 0.68 | 0.19 | 1.55 | 15.57 | 1.96 |
| C + 100 ALA | 3 | 1.12 | 0.09 | 1.05 | 1.22 | 28.40 | 13.72 |
| C + 300 ALA | 3 | 0.99 | 1.10 | 0.14 | 2.24 | 41.67 | 14.96 |
| OSM + carrier | 3 | 7.81 | 7.47 | 0.26 | 15.20 | 51.70 | 28.49 |
| OSM + 100 ALA | 3 | 8.50 | 4.36 | 4.09 | 12.80 | 28.80 | 4.96 |
| OSM + 300 ALA | 3 | 6.42 | 2.73 | 3.44 | 8.80 | 55.23 | 30.31 |

**not analyzed

As shown in Table 2, EPA but not ALA or DHA significantly decreased GAG release in OSM treated cultures. There was no significant effect on media lactate concentration by any dose of any of the fatty acids.

TABLE 3

Results for Dog 3

| Treatment | n | GAG release | | | | lactate | |
|---|---|---|---|---|---|---|---|
| | | mean | SD | min | max | mean | SD |
| C + carrier | 3 | 2.73 | 0.87 | 2.01 | 3.69 | 26.33 | 4.37 |
| C + 100 ALA | 3 | 2.12 | 0.43 | 1.81 | 2.61 | 24.40 | 4.00 |
| C + 100 DHA | 3 | 1.90 | 0.83 | 1.28 | 2.84 | 29.35 | 5.73 |
| C + 100 EPA | 3 | 1.67 | 0.41 | 1.30 | 2.11 | 36.10 | NA** |
| C + 300 ALA | 3 | 2.45 | 0.32 | 2.14 | 2.18 | 20.75 | 7.00 |
| C + 300 DHA | 3 | 1.55 | 0.73 | 0.73 | 2.13 | 28.40 | 0.57 |
| C + 300 EPA | 3 | 1.57 | 0.39 | 1.30 | 2.01 | 10.53 | 10.85 |
| RA + carrier | 3 | 20.82 | 0.65 | 20.10 | 21.37 | 38.47 | 4.78 |

TABLE 3-continued

Results for Dog 3

| Treatment | n | GAG release | | | | lactate | |
| --- | --- | --- | --- | --- | --- | --- | --- |
| | | mean | SD | min | max | mean | SD |
| RA + 100 ALA | 3 | 20.44 | 0.90 | 19.40 | 21.02 | 43.23 | 2.28 |
| RA + 100 DHA | 3 | 21.09 | 6.88 | 13.38 | 26.60 | 45.67 | 8.00 |
| RA + 100 EPA | 3 | 16.22 | 6.65 | 8.61 | 20.93 | 41.53 | 2.52 |
| RA + 300 ALA | 3 | 24.47 | 2.99 | 21.10 | 26.80 | 44.73 | 4.82 |
| RA + 300 DHA | 3 | 19.46 | 2.39 | 17.28 | 22.00 | 47.97 | 9.14 |
| RA + 300 EPA | 3 | 1.54 | 0.62 | 1.08 | 2.24 | NA** | NA** |
| OSM + carrier | 3 | 12.77 | 5.85 | 6.36 | 17.80 | 37.87 | 11.55 |
| OSM − 100 ALA | 3 | 22.03 | 4.60 | 18.40 | 27.20 | 32.77 | 1.82 |
| OSM − 100 DHA | 3 | 11.67 | 6.01 | 5.50 | 17.50 | 32.27 | 11.47 |
| OSM − 100 EPA | 3 | 17.85 | 2.05 | 16.40 | 19.30 | 39.05 | 11.53 |
| OSM − 300 ALA | 3 | 23.47 | 3.10 | 20.30 | 26.50 | 34.03 | 1.38 |
| OSM − 300 DHA | 3 | 11.63 | 5.07 | 6.79 | 16.90 | 30.00 | 5.96 |
| OSM − 300 EPA | 3 | 8.10 | 6.77 | 3.79 | 15.90 | 21.47 | 1.93 |

**not analyzed

As shown in Table 3, none of the fatty acids significantly altered GAG release from RA- or OSM-stimulated cartilage in this particular animal. There was no change in media lactate associated with any dose of any fatty acid.

TABLE 4

Results for Dog 4

| Treatment | n | GAG release | | | | lactate | |
| --- | --- | --- | --- | --- | --- | --- | --- |
| | | mean | SD | min | max | mean | SD |
| C + carrier | 3 | 1.96 | 0.53 | 1.51 | 2.55 | 22.93 | 4.75 |
| C + 100 ALA | 3 | 2.10 | 0.11 | 1.98 | 2.17 | 20.53 | 3.48 |
| C + 100 DHA | 3 | 2.34 | 0.33 | 2.00 | 2.66 | 19.10 | 2.35 |
| C + 100 EPA | 3 | 2.69 | 1.00 | 1.72 | 3.71 | 23.00 | 6.18 |
| C + 300 ALA | 3 | 1.53 | 1.24 | 0.13 | 2.50 | 29.17 | 22.07 |
| C + 300 DHA | 3 | 2.31 | 0.36 | 1.93 | 2.65 | 24.93 | 3.40 |
| C + 300 EPA | 3 | 2.10 | 0.45 | 1.64 | 2.55 | 24.77 | 13.00 |
| RA + carrier | 3 | 14.11 | 3.89 | 9.64 | 16.70 | 34.53 | 12.37 |
| RA + 100 ALA | 3 | 12.55 | 6.35 | 5.94 | 18.60 | 39.93 | 11.59 |
| RA + 100 DHA | 3 | 11.28 | 7.12 | 4.79 | 18.90 | 25.60 | 11.77 |
| RA + 100 EPA | 3 | 14.39 | 2.90 | 11.23 | 16.93 | 32.97 | 4.22 |
| RA + 300 ALA | 3 | 14.09 | 6.14 | 8.98 | 20.90 | 59.37 | 31.17 |
| RA + 300 DHA | 3 | 11.30 | 6.82 | 3.50 | 16.10 | 25.33 | 11.68 |
| RA + 300 EPA | 3 | 9.09 | 1.32 | 8.26 | 10.61 | 25.10 | 4.67 |
| OSM + carrier | 3 | 16.08 | 3.54 | 12.05 | 18.70 | 31.20 | 5.99 |
| OSM + 100 ALA | 3 | 11.70 | 2.19 | 9.43 | 13.80 | 26.33 | 9.25 |
| OSM + 100 DHA | 3 | 24.97 | 3.26 | 21.20 | 26.90 | 36.83 | 5.07 |
| OSM + 100 EPA | 3 | 15.88 | 4.32 | 11.95 | 20.50 | 27.24 | 6.34 |
| OSM + 300 ALA | 3 | 19.56 | 3.91 | 15.50 | 23.30 | 26.67 | 6.10 |
| OSM + 300 DHA | 3 | 16.40 | 6.27 | 9.40 | 21.50 | 36.23 | 20.34 |
| OSM + 300 EPA | 3 | 13.49 | 5.75 | 7.54 | 19.02 | 27.80 | 2.72 |

As shown in Table 4, EPA at 300 μg/ml, but not any other fatty acid at any dose, significantly decreased GAG release from RA treated cultures. There was a significant decrease in media lactate concentration in control, RA- and OSM-treated cultures with the 300 μg/ml OSM pre-treatment.

Example 2

This example illustrates the incorporation of omega-3 fatty acids into canine chondrocyte membranes.

The majority of these experiments were performed using monolayer cultures, however, in a single experiment, the incorporation of fatty acids into explant cultures of canine cartilage was analyzed.

Monolayer Cultures

Over 24 or 48 hours there was no incorporation of the 18:3 omega-3 fatty acid ALA into chondrocyte membranes from two dogs. The percentage of ALA in chondrocytes incubated in medium alone was <1% out of 5 (range 0.3-0.9%) and after 24 or 48 hours of incubation with 100 or 300 μg/ml ALA this percentage had not significantly changed (range 0.3-2.5%).

Over 48 hours there was significant incorporation of the 20:5 omega-3 fatty acid EPA into chondrocyte membranes from one dog. The percentage of EPA increased from <1% (range 0.2-0.6%) to approximately 7% (range 5.6-8%) when cultures were treated with 100 or 300 μg/ml EPA for 48 hours. The incorporation was not different when cultures were performed in the presence or absence of 5% fetal calf serum (FCS).

Over 48 hours there was significant incorporation of the 20:5 omega-3 fatty acid EPA but not the 18:3 omega-3 fatty acid ALA into chondrocyte membranes from one dog (doses of 300 μg/ml for each fatty acid). The percentage of EPA increased from <1% to approximately 15%.

Over 3 or 6 days there was significant incorporation of the 20:5 omega-3 fatty acid EPA into chondrocyte membranes from one dog (dose of 300 μg/ml EPA). The percentage of EPA increased from <1% to 16-18% with no difference between 3 and 6 days incubation.

Explant Culture

Over 6 days there was apparent incorporation of the 20:5 omega-3 fatty acid EPA, but not the 18:3 omega-3 fatty acid DHA or the omega-6 fatty acid AA into cartilage explants from one dog (dose of 300 μg/ml for each fatty acid). The percentage of EPA increased from 0% (none detectable) to approximately 2%.

SUMMARY

These data indicated that EPA, but no other omega-3 fatty acid, was incorporated into canine chondrocyte membranes in either monolayer or explant cultures.

Example 3

This example illustrates the effect of omega-3 fatty acids on canine chondrocyte metabolism.

To assess the potential effect of omega-3 fatty acids on protein and proteoglycan metabolism in canine cartilage, cultures were set up as described in Example 1 except for the final 4 days of culture, when no catabolic stimuli were added (i.e., all "control" cultures). During the final 24 hours of culture (i) $^{35}SO_4$ (to measure proteoglycan synthesis) or (ii) $^{35}S$-methionine and $^{35}S$-cysteine (to measure protein synthesis) were added to the medium to radiolabel newly synthesized proteoglycans and proteins, respectively. The incorporation of radiolabel into the cartilage matrix was measured at the termination of culture. No attempt was made to quantitate loss of radiolabeled material from the cartilage over the 24-hour labeling period. The mean and standard deviation (SD) of the incorporation of $^{35}SO_4$ ("PG") or $^{35}S$-methionine and $^{35}S$-cysteine ("PROT") as DPM/mg wet weight are shown in Table 5 below.

TABLE 5

| Treatment | n | PG | | PROT | |
| --- | --- | --- | --- | --- | --- |
| | | mean | SD | mean | SD |
| Carrier | 3 | 292.7 | 53.1 | 574.3 | 198.3 |
| 100 ALA | 3 | 246.3 | 100.8 | 503.7 | 184.2 |
| 100 DHA | 3 | 156.0 | 82.5 | 503.7 | 81.34 |
| 100 EPA | 3 | 537.3 | 161.8 | 442.0 | 72.7 |
| 300 ALA | 3 | 443.0 | 205.4 | 393.7 | 35.0 |

TABLE 5-continued

|  |  | PG | | PROT | |
| --- | --- | --- | --- | --- | --- |
| Treatment | n | mean | SD | mean | SD |
| 300 DHA | 3 | 123.3 | 38.2 | 564.3 | 220.0 |
| 300 EPA | 3 | 275.7 | 161.7 | 504.0 | 44.5 |

As shown in Table 5, there was no significant effect of any omega-3 fatty acid on protein synthesis and incorporation into the matrix. EPA at 100 µ/ml significantly increased proteoglycan synthesis and incorporation. No other dose or fatty acid significantly altered proteoglycan synthesis and incorporation into the cartilage matrix.

Reverse transcription-PCR was used to measure the mRNA message expression levels of matrix proteinases (aggrecanases-1 and -2), cyclooxygenases-1 and -2, lipoxygenases-5 and -12, and potential autocrine cytokines and their receptors (e.g., IL-1, IL-6 and TNF).

The results of this study found that aggrecanase-1 and aggrecanase-2 mRNA messages were expressed in "nomial" canine cartilage tissue. In addition, some dogs expressed mRNA message of cyclooxygenase-2 (COX-2) message although there were no signs of joint pathology in these animals. This enabled monitoring the effects of omega-3 and omega-6 fatty acid supplementation on mRNA expression of aggrecanases and COX-2 in unstimulated canine articular cartilage explants. EPA was the only fatty acid able to reduce the mRNA message for the degradative enzymes, aggrecanase-1 and aggrecanase-2, in canine articular cartilage. This demonstrated the ability of EPA to "turn off" the genes responsible for cartilage degradation.

Example 4

This example illustrates the effects of omega-3 fatty acids in canine osteoarthritis clinical studies.

Three clinical studies were conducted in pet dogs clinically diagnosed with osteoarthritis. Veterinary general practitioners and orthopedic specialists enrolled client owned dogs that met specific eligibility criteria. All patients were required to (i) have radiographic evidence of osteoarthritis with measurable clinical manifestations of disease, based on historical accounts by pet owners and physical examinations by veterinarians; (ii) be otherwise healthy and free of concurrent diseases based on physical exam, complete blood count (CBC), blood chemistry and urinalysis; and (iii) maintain regimen of therapy if receiving medications or supplements prescribed for osteoarthritis during the 30 days prior to enrolling in the study.

The following measurements were made.

Serum fatty acid profile. This was determined by a gas chromatography method involving extraction of fatty acids by chloroform and methanol mixture (2:1), methylation using boron trifluoride-methanol ($BF_3$:MeOH) reagent followed by flame ionization detection (FID). Fatty acid methyl esters were identified by comparison of retention times with those of known standards and quantitated using an internal standard.

Veterinary clinical evaluation. Veterinarians conducted both a physical exam and a clinical evaluation of the patient's osteoarthritic condition during the screening phase and at the conclusion of each of the feeding intervals over the course of the clinical trial. Veterinarians assessed the severity of five osteoarthritic parameters: lameness, reluctance to bear weight, reduction in range of motion, reluctance to hold up contra-lateral limb, and pain on palpation of the joint. Changes in severity scores for these individual parameters were measured over the duration of the feeding period. A comprehensive veterinary clinical assessment of the impact of dietary intervention on the osteoarthritic condition of patients was derived by combining the changes in severity scores for all five individual parameters.

Pet owner subjective evaluation. Pet owners were required to complete an enrollment questionnaire prior to participating in the study and additional questionnaires at the conclusion of each of the feeding intervals over the course of the clinical trial.

Enrollment questionnaire. Pet owners rated the observed frequency and severity of the most common signs of canine osteoarthritis including difficulty rising from rest, limping, stiffness, soreness when touched, lagging behind during walks, yelping or whimpering in pain, aggressive behaviors, difficulty in running, difficulty in walking, difficulty in climbing steps, difficulty in jumping, difficulty in playing, impaired mobility, and overall activity level. In addition, owners rated the overall osteoarthritic condition of their pet.

Feeding questionnaire. Pet owners rated both the frequency and change in severity of the signs of canine osteoarthritis which were benchmarked during enrollment. In addition, the pet owners rated the severity of their animal's pain associated with osteoarthritis.

Force plate gait analysis. Dogs were evaluated at each institution using a computerized biomechanics force plate at 0, 6 and 12 weeks. The plate was mounted centrally in and flush with the surface of a 10 m walkway. A handler trotted dogs across the force plate and an observer evaluated each pass across the plate to confirm foot-strikes and gait. A trial was considered valid if there were distinct ipsilateral fore foot and hind foot strikes while the dog was trotted across the force plate at a velocity of 1.7-2.0 m/s, with an acceleration variation of −0.5-0.5 m/s$^2$. During each trial, the dog's forward velocity was measured, using a millisecond timer and two photoelectric switches. Each trial was videotaped for review and confirmation of valid foot-strikes. Care was taken to ensure that the dog triggered the timer and that a consistent speed (as perceived by the handler and observer) was maintained across the plate during each trial.

Five valid trials for each test period were obtained for each affected limb and each ipsilateral limb of each dog. Orthogonal ground reaction forces of peak vertical force, vertical impulse, braking and propulsive peak forces, and braking and propulsion impulses were measured and recorded by a specialized software program. (Acquire, Sharon Software, DeWitt, Mich.), All forces were normalized with respect to body weight in kilograms. Data from the valid trial for each limb were averaged to obtain a mean value for each force or impulse at each time period.

Ground reaction force data were compared between treatment and placebo groups as a percentage difference between lame and ipsilateral limbs at each time period. Percentage change of ground force data on the lame limb were compared at the beginning and end of the feeding period.

Study #1

A canine study was conducted to evaluate the dietary effect of feeding increased levels of n-3 fatty acids to dogs diagnosed with osteoarthritis. Eighteen veterinary general practitioners were recruited to enroll patients in the study. A total of 131 dogs were randomly assigned to two dietary treatments and fed for 180 days. The test and control foods had similar macronutrient profile, but were significantly different in fatty acid composition (Table 6). The test diet contained high levels of ALA, EPA and DHA, and was formulated with a low n-6/n-3 ratio. The control diet was a leading selling commercially available dog food, with typical levels of n-3 fatty acids and an n-6/n-3 ratio characteristic for the industry.

TABLE 6

| Dietary nutrient | Control food (%) | Test food (%) |
| --- | --- | --- |
| Protein | 23.2 | 19.9 |
| Fat (total) | 13.9 | 13.6 |
| $CHO_2$ (NFE*) | 54.7 | 53.3 |
| ALA (n-3) | 0.12 | 2.8 |
| AA (n-6) | 0.03 | 0.06 |
| EPA (n-3) | <0.01 | 0.38 |
| DHA (n-3) | <0.01 | 0.31 |
| Sum n-6 | 1.99 | 2.53 |
| Sum n-3 | 0.09 | 3.48 |
| n6/n3 ratio | 22.8 | 0.7 |

*NFE = Soluble carbohydrate content as nitrogen free extract

Serum fatty acids and pet owner evaluations were recorded at 0, 45, 90 and 180 days. Serum fatty acid profiles were significantly modulated by the test food. The test group had significantly higher concentrations of n-3 fatty acids ($P<0.01$), specifically EPA, DHA and ALA, significantly lower concentrations of AA ($P<0.01$), and significantly lower n-6/n-3 ratios ($P<0.01$) as compared to the control group at the conclusion of each feeding interval (Table 7). The test group showed significant improvements for rising from rest, running and playing at day 45 and walking at days 90 and 180 as compared to the control group based on pet owner observations ($P<0.05$), even in the presence of a strong placebo effect (Table 8).

TABLE 7

| | Mean serum fatty acid levels (mg/dl) | | | |
| --- | --- | --- | --- | --- |
| | Group | Day 0 | Day 45 | Day 90 | Day 180 |
| ALA (n-3) | Control | 1.10 | 0.89 | 0.52 | 0.53 |
| | Test | 1.05 | 5.61 | 6.51 | 7.13 |
| AA (n-6) | Control | 71.35 | 66.34 | 68.03 | 68.21 |
| | Test | 64.32 | 45.90 | 46.13 | 42.65 |
| EPA (n-3) | Control | 1.14 | 0.90 | 0.67 | 0.93 |
| | Test | 1.28 | 16.28 | 18.64 | 19.94 |
| DHA (n-3) | Control | 2.67 | 2.03 | 1.70 | 1.98 |
| | Test | 2.93 | 11.31 | 12.24 | 12.17 |
| Sum n-6 | Control | 141.08 | 138.72 | 137.85 | 140.28 |
| | Test | 130.85 | 118.87 | 128.71 | 123.99 |
| Sum n-3 | Control | 4.95 | 3.84 | 2.93 | 3.51 |
| | Test | 5.36 | 33.20 | 37.39 | 39.24 |
| n-6/n-3 ratio | Control | 33.33 | 37.95 | 51.59 | 51.39 |
| | Test | 33.90 | 7.47 | 8.63 | 6.92 |

TABLE 8

| | | Day 0-45 | | Day 45-90 | | Day 90-180 | |
| --- | --- | --- | --- | --- | --- | --- | --- |
| Osteoarthritic sign | Group | mean | P value | mean | P value | mean | P value |
| Rising from rest | Control | 1.77 | .041 | 1.77 | nsd** | 1.93 | nsd** |
| | Test | 1.56 | | 1.84 | | 1.91 | |
| Running | Control | 1.81 | .037 | 1.83 | nsd** | 1.94 | nsd** |
| | Test | 1.56 | | 1.71 | | 1.91 | |
| Walking | Control | 1.71 | nsd** | 2.00 | .018 | 2.19 | .002 |
| | Test | 1.69 | | 1.71 | | 1.75 | |
| Playing | Control | 1.83 | .008 | 1.90 | nsd** | 2.06 | nsd** |
| | Test | 1.50 | | 1.78 | | 1.97 | |

*Osteoarthritis severity rating scale: 1 = better, 2 = no change, 3 = worsened.
**nsd = no significant difference.

Study #2

A canine study was conducted to evaluate the dietary effect of feeding increased levels of n-3 fatty acids to dogs diagnosed with osteoarthritis. Two veterinary orthopedic specialists enrolled patients in the study. A total of 38 dogs were randomly assigned to two dietary treatments and fed for 90 days. The test and control diets were manufactured from the same lots of foods as described above (Table 6).

Serum fatty acids, force plate gait analysis, and veterinary clinical assessments were recorded at 0, 45 and 90 days. Serum fatty acid profiles were significantly modulated by the test food. The test group had significantly higher serum concentrations of n-3 fatty acids ($P<0.01$), specifically EPA, DHA and ALA, significantly lower concentrations of AA at day 90 ($P<0.01$), and significantly lower n-6/n-3 ratios ($P<0.01$) as compared to the control group at the conclusion of each feeding interval (Table 9).

TABLE 9

Mean serum fatty acid levels (mg/dl)

| | | Day 0 | | Day 45 | | Day 90 | |
|---|---|---|---|---|---|---|---|
| | Group | mean | P value | mean | P value | mean | P value |
| ALA (n-3) | Control | 0.89 | 0.7764 | 0.34 | <0.0001 | 0.27 | <0.0001 |
| | Test | 0.98 | | 4.45 | | 5.04 | |
| AA (n-6) | Control | 55.55 | 0.6880 | 50.78 | 0.0736 | 55.95 | 0.0001 |
| | Test | 57.13 | | 41.94 | | 38.01 | |
| EPA (n-3) | Control | 1.19 | 0.7000 | 0.34 | <0.0001 | 0.20 | <0.0001 |
| | Test | 1.54 | | 11.52 | | 11.89 | |
| DHA (n-3) | Control | 4.30 | 0.4323 | 1.82 | <0.0001 | 1.32 | <0.0001 |
| | Test | 3.37 | | 11.15 | | 11.21 | |
| Sum n-6 | Control | 122.85 | 0.2508 | 112.46 | 0.0148 | 114.60 | 0.0036 |
| | Test | 113.61 | | 91.72 | | 89.85 | |
| Sum n-3 | Control | 6.36 | 0.8335 | 2.57 | <0.0001 | 1.79 | <0.0001 |
| | Test | 5.90 | | 27.14 | | 28.13 | |
| n-6/n-3 ratio | Control | 32.54 | 0.2521 | 66.66 | <0.0001 | 75.90 | <0.0001 |
| | Test | 45.90 | | 8.48 | | 3.59 | |

A biomechanical assessment of the dogs' most severe osteoarthritic limb was objectively evaluated using force plate gait analysis (Table 10). Vertical peak force is the key parameter measured to determine weight bearing of the affected limb. There was no significant change in mean vertical peak force over the duration of the 90 day feeding for the control group (P=0.91), while there was a significant increase in mean vertical peak force over time for the test group (P=0.01). The percent mean change in vertical peak force was also significantly different between groups (P<0.05), indicating that the test group increased weight bearing in the affected limb, while the control group displayed no change in weight bearing over the course of the study. Weight bearing ability can also be represented by displaying the frequency distribution of percent change in vertical peak for each dietary group. Only 31% of animals in the control group showed improvement in weight bearing after the 90 day feeding, while 82% of the dogs in the test group increased weight bearing over the course of the study.

TABLE 10

Vertical peak force

| | Day 0 | | Day 90 | | Change (Day 0-90) | | | |
|---|---|---|---|---|---|---|---|---|
| Group | mean | P value | mean | P value | mean change | mean = 0 Pr > \|t\| | % mean change | Pr > \|t\| |
| Control | 72.80 | 0.5981 | 72.63 | 0.9323 | -0.17 | 0.9144 | -0.58 | 0.0443 |
| Test | 69.51 | | 73.21 | | 3.71 | 0.0103 | 5.35 | |

The subjective clinical evaluations performed by the veterinary orthopedic surgeons provided additional support for the efficaciousness of the test diet. Based upon the comprehensive veterinary clinical assessment, a significantly greater percent of dogs were evaluated as improved that consumed the test food as compared to dogs that consumed the control food (P<0.05). The veterinary specialists also observed a greater percent of dogs in the test group displaying a reduction in pain on palpation of the joint as compared to the control group (P=0.05).

Study #3

A canine study was conducted to determine the dose effect of feeding increased levels of n-3 fatty acids to dogs diagnosed with osteoarthritis. Twenty-eight veterinary general practitioners enrolled patients in the study. A total of 177 dogs were randomly assigned to three dietary treatments and fed for 90 days. Approximately two-thirds of the dogs participating in the study were receiving medications and/or supplements prescribed for treating osteoarthritis, in addition to consuming the therapeutic diets being evaluated. The three test foods had similar macronutrient profiles, but varied in composition of EPA and DHA, with variable A containing the lowest levels and variable C containing the highest levels (Table 11).

TABLE 11

| | Test variable % | | |
|---|---|---|---|
| Dietary nutrient | A | B | C |
| Protein | 19.97 | 19.51 | 19.37 |
| Fat (total) | 13.78 | 15.34 | 19.55 |
| CHO$_2$ (NFE*) | 53.92 | 52.34 | 47.66 |
| ALA (n-3) | 2.65 | 1.18 | 1.10 |
| AA (n-6) | 0.11 | 0.18 | 0.24 |

TABLE 11-continued

| | Test variable % | | |
|---|---|---|---|
| Dietary nutrient | A | B | C |
| EPA (n-3) | 0.50 | 1.18 | 1.69 |
| DHA (n-3) | 0.34 | 0.80 | 1.15 |
| Sum n-6 | 2.70 | 2.45 | 2.14 |
| Sum n-3 | 3.54 | 3.53 | 4.52 |
| n-6/n-3 ratio | 0.76 | 0.70 | 0.47 |

*NFE = Soluble carbohydrate content as nitrogen free extract

Serum fatty acids, pet owner evaluations, and veterinary clinical assessments were recorded at 0, 21, 45 and 90 days. Serum fatty acid profiles were significantly modulated by all dietary variables. The dogs fed test variables B & C had significantly higher serum concentrations of n-3 fatty acids (P<0.01), specifically EPA, DHA and ALA, significantly lower concentrations of n-6 fatty acids, specifically AA (P<0.01), and significantly lower n-6/n-3 ratios (P<0.01) as compared to the dogs fed test variable A at the conclusion of each feeding interval (Table 12).

TABLE 12

Mean serum fatty acid levels (mg/dl)

| | Test variable | Day 0 | Day 21 | Day 45 | Day 90 |
|---|---|---|---|---|---|
| ALA (n-3) | A | 1.34 | 5.65 | 5.29 | 5.63 |
| | B | 1.29 | 3.36 | 3.99 | 3.82 |
| | C | 1.25 | 2.92 | 3.32 | 3.29 |
| AA (n-6) | A | 76.37 | 51.10 | 47.54 | 47.77 |
| | B | 73.15 | 41.55 | 38.94 | 37.00 |
| | C | 70.05 | 37.35 | 36.86 | 34.73 |
| EPA (n-3) | A | 1.32 | 18.74 | 18.51 | 19.26 |
| | B | 1.54 | 26.14 | 29.87 | 30.03 |
| | C | 1.85 | 34.42 | 35.71 | 39.04 |
| DHA (n-3) | A | 3.50 | 13.75 | 13.84 | 13.88 |
| | B | 4.72 | 18.47 | 19.98 | 20.16 |
| | C | 3.91 | 21.01 | 21.47 | 22.49 |
| Sum n-6 | A | 150.38 | 114.38 | 110.12 | 112.70 |
| | B | 143.93 | 93.83 | 95.87 | 92.10 |
| | C | 139.97 | 79.71 | 82.65 | 80.74 |
| Sum n-3 | A | 6.16 | 38.14 | 37.65 | 38.77 |
| | B | 7.55 | 47.96 | 53.84 | 54.01 |
| | C | 7.01 | 58.35 | 60.50 | 68.83 |
| n-6/n-3 ratio | A | 29.99 | 5.65 | 3.48 | 3.75 |
| | B | 28.09 | 3.36 | 1.92 | 1.79 |
| | C | 32.30 | 2.92 | 2.02 | 1.73 |

Pet owners reported improvements in 13 of 14 individual osteoarthritic signs for dogs consuming any of the dietary variables for 21 days (Table 13). Additionally, pet owners reported a decrease in severity for 13 of 14 individual osteoarthritic signs for dogs consuming any of the dietary variables for 90 days (Table 14). Pet owners also reported a significant reduction in the frequency of observable osteoarthritic signs after the dogs consumed any of the dietary variables for 90 days (Table 15).

TABLE 13

Pet owner observed improvements in osteoarthritic signs (Day 0-21)

| Osteoarthritic Sign | Diet | Mean | Mean = 0 Pr > \|t\| |
|---|---|---|---|
| Rising from rest | A | −0.439 | 0.0002 |
| | B | −0.738 | <0.0001 |
| | C | −0.763 | <0.0001 |
| Limping | A | −0.720 | <0.0001 |
| | B | −0.731 | <0.0001 |
| | C | −0.837 | <0.0001 |
| Stiffness | A | −0.537 | <0.0001 |
| | B | −0.783 | <0.0001 |
| | C | −0.627 | <0.0001 |
| Soreness | A | −0.750 | 0.0005 |
| | B | −0.800 | 0.0002 |
| | C | −0.379 | 0.0451 |
| Lagging behind on walks | A | −0.564 | 0.0004 |
| | B | −0.909 | <0.0001 |
| | C | −0.531 | 0.0022 |
| Pain | A | −0.476 | 0.0245 |
| | B | −0.478 | 0.0184 |
| | C | −0.889 | 0.0002 |
| Aggression | A | 0.000 | 1.0000 |
| | B | −0.313 | 0.1050 |
| | C | −0.429 | 0.1401 |
| Running | A | −0.524 | 0.0004 |
| | B | −0.682 | <0.0001 |
| | C | −0.674 | <0.0001 |
| Walking | A | −0.553 | 0.0007 |
| | B | −0.750 | <0.0001 |
| | C | −0.667 | <0.0001 |
| Stair climbing | A | −0.449 | 0.0012 |
| | B | −0.667 | <0.0001 |
| | C | −0.723 | <0.0001 |
| Jumping | A | −0.362 | 0.0049 |
| | B | −0.600 | <0.0001 |
| | C | −0.542 | <0.0001 |
| Playing | A | −0.622 | <0.0001 |
| | B | −0.763 | <0.0001 |
| | C | −0.487 | 0.0014 |
| Impaired mobility | A | −0.528 | 0.0005 |
| | B | −0.700 | <0.0001 |
| | C | −0.564 | 0.0001 |
| Activity level | A | −0.745 | <0.0001 |
| | B | −0.857 | <0.0001 |
| | C | −0.865 | <0.0001 |

The above "p" values refer to the mean change from day 0 to day 21.

TABLE 14

Difference in pet owners' severity rating (Day 0-90)

| Osteoarthritic Sign | Diet | Mean | Pr > t |
|---|---|---|---|
| Rising from rest | A | −0.463 | <0.0001 |
| | B | −0.633 | <0.0001 |
| | C | −0.518 | <0.0001 |
| Limping | A | −0.489 | 0.0003 |
| | B | −0.588 | <0.0001 |
| | C | −0.681 | <0.0001 |
| Stiffness | A | −0.255 | 0.0420 |
| | B | −0.483 | <0.0001 |
| | C | −0.589 | <0.0001 |
| Soreness | A | −0.810 | <0.0001 |
| | B | −0.920 | <0.0001 |
| | C | −0.926 | <0.0001 |
| Lagging behind on walks | A | −0.657 | <0.0001 |
| | B | −0.531 | 0.0014 |
| | C | −0.448 | 0.0094 |
| Pain | A | −0.684 | 0.0002 |
| | B | −0.571 | 0.0009 |
| | C | −0.667 | 0.0010 |
| Aggression | A | −0.750 | 0.0234 |
| | B | −1.000 | 0.0025 |
| | C | −1.000 | 0.0751 |
| Running | A | −0.579 | <0.0001 |
| | B | −0.558 | <0.0001 |
| | C | −0.605 | <0.0001 |
| Walking | A | −0.294 | 0.0358 |
| | B | −0.643 | <0.0001 |
| | C | −0.595 | <0.0001 |
| Stair climbing | A | −0.419 | 0.0024 |
| | B | −0.489 | 0.0002 |
| | C | −0.689 | <0.0001 |
| Jumping | A | −0.571 | 0.0003 |
| | B | −0.479 | 0.0011 |
| | C | −0.773 | <0.0001 |
| Playing | A | −0.606 | 0.0002 |
| | B | −0.571 | 0.0003 |
| | C | −0.694 | <0.0001 |
| Lameness | A | −0.484 | 0.0045 |
| | B | −0.778 | <0.0001 |
| | C | −0.667 | <0.0001 |
| Activity level | A | −0.409 | 0.0009 |
| | B | −0.704 | <0.0001 |
| | C | −0.551 | <0.0001 |

The above "p" values refer to the mean change from day 0 to day 90.

TABLE 15

Difference in pet owners' frequency rating (Day 0-90)

| Osteoarthritic Sign | Diet | Mean | Pr > t |
|---|---|---|---|
| Rising from rest | A | −0.370 | <0.0001 |
| | B | −0.467 | <0.0001 |
| | C | −0.509 | <0.0001 |
| Stiffness | A | −0.098 | 0.2929 |
| | B | −0.373 | <0.0001 |
| | C | −0.421 | <0.0001 |
| Soreness | A | −0.381 | 0.0146 |
| | B | −0.680 | <0.0001 |
| | C | −0.821 | <0.0001 |
| Running | A | −0.447 | 0.0004 |
| | B | −0.395 | 0.0009 |
| | C | −0.477 | <0.0001 |
| Jumping | A | −0.357 | 0.0027 |
| | B | −0.354 | 0.0015 |
| | C | −0.467 | <0.0001 |
| Playing | A | −0.455 | 0.0013 |
| | B | −0.297 | 0.0238 |
| | C | −0.667 | 0.0010 |
| Limping | A | −0.239 | <0.0165 |
| | B | −0.365 | <0.0001 |
| | C | −0.396 | <0.0001 |
| Lagging behind on walks | A | −0.571 | <0.0001 |
| | B | −0.643 | <0.0001 |
| | C | −0.500 | 0.0004 |
| Aggression | A | −0.417 | 0.0536 |
| | B | −0.467 | 0.0175 |
| | C | −0.167 | 0.5741 |
| Walking | A | −0.206 | 0.0911 |
| | B | −0.558 | <0.0001 |
| | C | −0.447 | 0.0002 |
| Stair climbing | A | −0.302 | 0.0069 |
| | B | −0.348 | 0.0014 |
| | C | −0.457 | <0.0001 |
| Impaired mobility | A | −0.250 | 0.0643 |
| | B | −0.436 | 0.0005 |
| | C | −0.667 | <0.0001 |

Dogs consuming higher concentrations of n-3 fatty acids were reported to have more significant improvement in osteoarthritic condition and more significant reduction in the progression of osteoarthritis than those dogs receiving the lowest dosage, based on veterinarians clinical assessments (Table 16). There was no significant difference in improvement in osteoarthritic condition or reduction in the progression of osteoarthritis between the group receiving medications and/or supplements and the non-medicated group (Table 17). This indicates that the therapeutic diets work synergistically with other therapies or at least not withstanding other therapies by providing additional benefit to dogs suffering from osteoarthritis.

An extremely low incidence of adverse reactions or side effects was reported among dogs participating in this study. Only five dogs out of the 215 animals assigned to food were reported to have diarrhea and vomiting, which could possibly be attributed to consuming one of the dietary variables. Similar incidence of adverse reactions or side effects were reported for those dogs consuming the therapeutic diets in the previous two studies discussed (1/88 and 1/26 for examples 1 and 2 respectively).

TABLE 16

| | Progression of osteoarthritic condition | | | | Overall change in osteoarthritic condition | | | |
|---|---|---|---|---|---|---|---|---|
| Diet | n | mean | P | | Diet | n | mean | P |
| A | 55 | 2.327 | 0.2891 | A vs B | A | 54 | 3.148 | 0.1675 | A vs B |
| B | 62 | 2.177 | 0.1619 | B vs C | B | 62 | 2.871 | 0.0787 | B vs C |
| C | 59 | 1.983 | 0.0168 | A vs C | C | 59 | 2.525 | 0.0024 | A vs C |

TABLE 17

| | | Progression of osteoarthritic condition | | | | | Overall change in osteoarthritic condition | | |
|---|---|---|---|---|---|---|---|---|---|
| Diet | Medicated | n | mean | P | Diet | Medicated | n | mean | P |
| A | no | 22 | 2.273 | 0.6665 | A | no | 21 | 3.143 | 0.9770 |
| | yes | 33 | 2.364 | | | yes | 33 | 3.152 | |
| B | no | 23 | 2.130 | 0.7109 | B | no | 23 | 2.696 | 0.3247 |
| | yes | 39 | 2.205 | | | yes | 39 | 2.974 | |
| C | no | 28 | 2.071 | 0.4003 | C | no | 28 | 2.750 | 0.1285 |
| | yes | 31 | 1.903 | | | yes | 31 | 2.323 | |

All patents and publications cited herein are incorporated by reference into this application in their entirety.

The words "comprise", "comprises", and "comprising" are to be interpreted inclusively rather than exclusively.

What is claimed is:

1. A method for reducing pain associated with arthritis in a dog in need thereof, the method comprising administering to the dog a food composition comprising:
   eicosapentaenoic acid at a concentration within a range of from about 0.4 wt. % to about 5.0 wt. %
   a total omega-3 fatty acid content within a range of from about 3.5 wt. % to about 8.0 wt. % on a dry matter basis; and at least one of an omega-6 fatty acid, wherein the ratio of total omega-3 fatty acids to total omega-6 fatty acids is 1 of omega-3 fatty acids to about 0.8 to about 0.2 of omega-6 fatty acids.

2. The method of claim 1, wherein one or more genes responsible for cartilage degradation are down-regulated.

3. The method of claim 1, wherein one or more genes responsible for cartilage degradation are turned off.

4. The method of claim 1, wherein mRNA message expression in cartilage tissue of the dog for an enzyme causing cartilage degradation is reduced.

5. The method of claim 4, wherein the enzyme is aggrecanase.

6. The method of claim 1, wherein induced release of glycosaminoglycan from cartilage tissue of the dog is decreased.

* * * * *